United States Patent [19]

Lübbers et al.

[11] Patent Number: 5,353,792
[45] Date of Patent: Oct. 11, 1994

[54] SENSING DEVICE

[75] Inventors: Dietrich W. Lübbers, Dortmund, Fed. Rep. of Germany; Hellfried Karpf, Graz, Austria

[73] Assignee: AVL Medical Instruments AG, Schaffhausen, Switzerland

[21] Appl. No.: 96,409

[22] Filed: Jul. 26, 1993

[30] Foreign Application Priority Data

Sep. 25, 1992 [AT] Austria .............................. A 1914/92

[51] Int. Cl.⁵ .............................................. A61B 5/00
[52] U.S. Cl. .................................... 128/634; 436/172
[58] Field of Search ............................... 128/632–635, 128/664–647; 356/39–41; 436/68, 172

[56] References Cited

U.S. PATENT DOCUMENTS

| | | | |
|---|---|---|---|
| 3,604,927 | 9/1971 | Hirschfeld . | |
| 4,706,677 | 11/1987 | Goorsky et al. | 128/634 |
| 4,730,622 | 3/1988 | Cohen | 128/667 |
| 4,803,992 | 2/1989 | Lemelson | 128/634 |
| 4,889,407 | 12/1989 | Markle et al. | 128/634 X |
| 5,005,576 | 4/1991 | Gunther | 128/634 |
| 5,054,882 | 10/1991 | Riccitelli et al. | 128/634 X |
| 5,119,463 | 6/1992 | Vurek et al. | 128/634 X |
| 5,173,432 | 12/1992 | Lefkowitz | 128/635 X |
| 5,244,636 | 9/1993 | Walt et al. | 128/634 X |

FOREIGN PATENT DOCUMENTS 392539 4/1991 Austria .
3532563 6/1980 Fed. Rep. of Germany .

OTHER PUBLICATIONS

P. Lönnroth et al., "A Microdialysis Method . . . in Humans" in American Physiological Society, 1987, pp. 228–231.

Primary Examiner—Angela D. Sykes
Attorney, Agent, or Firm—Watson, Cole, Grindle & Watson

[57] ABSTRACT

In order to simultaneously determine the concentrations of different analytes in several places in a tissue by means of a thin, biocompatible tube or cannula which is inserted into the tissue, the tube is provided with several areas along its length which contain either identical or different optically excitable and readable, preferably luminescence-optical, indicating substances for measuring the local distribution of one parameter, such as $O_2$ concentration or $O_2$ partial pressure, or for simultaneous measurement of at least two different parameters, e.g., $pO_2$, $pCO_2$ or pH.

16 Claims, 2 Drawing Sheets

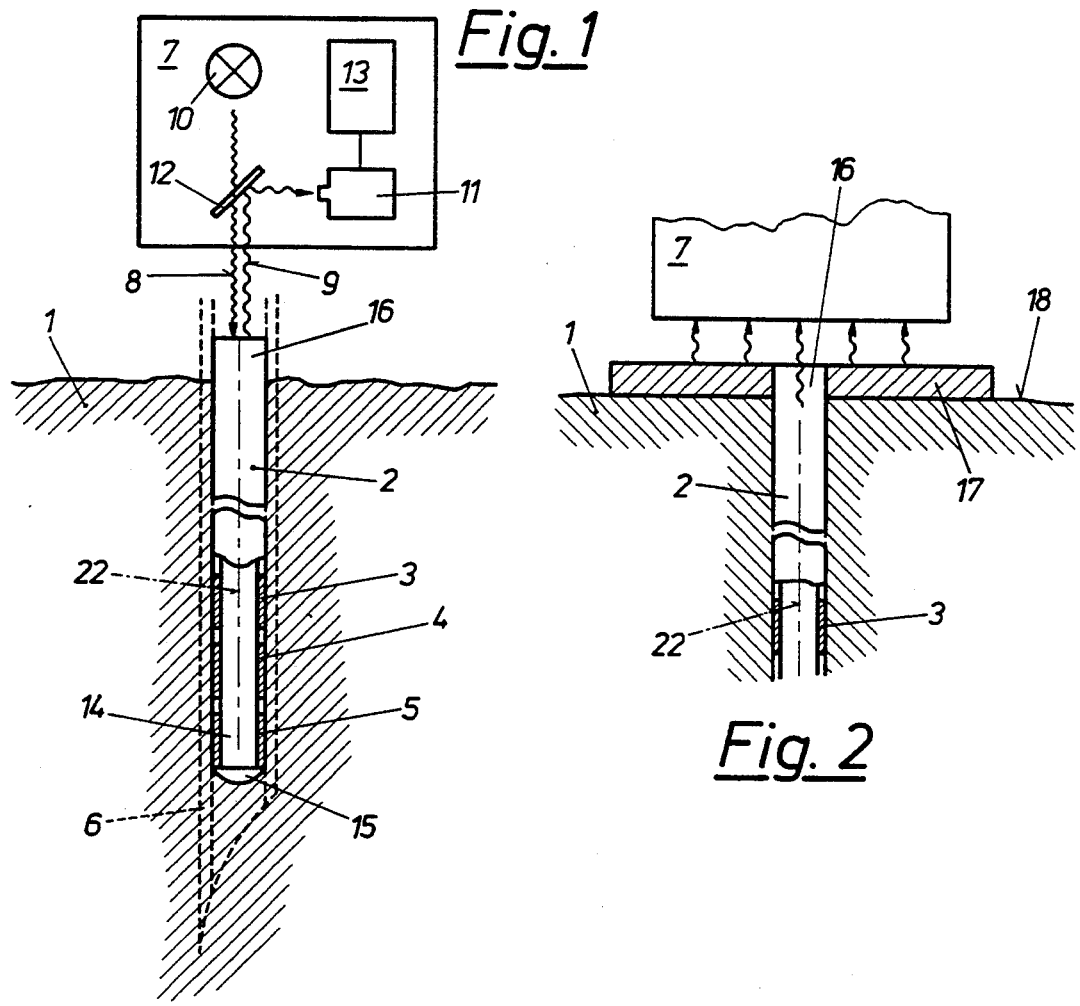
Fig. 1
Fig. 2
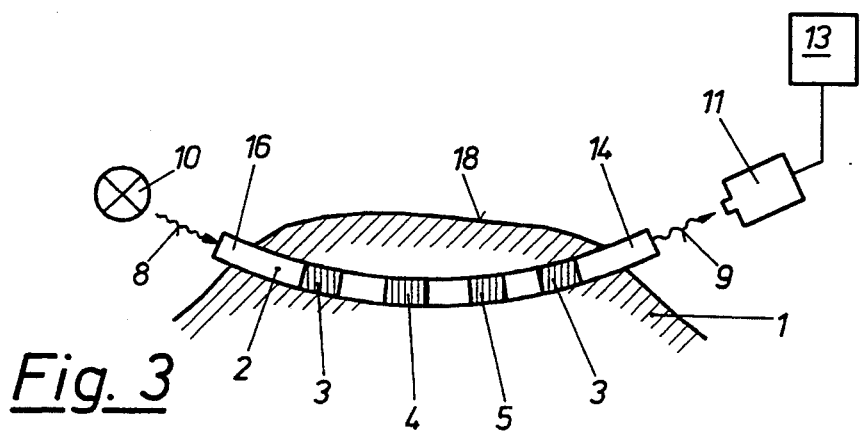
Fig. 3

SENSING DEVICE

BACKGROUND OF THE INVENTION

The invention relates to a sensing device comprising a thin biocompatible cannula or tube which may be inserted into human or animal tissue, such as a microdialysis tube, measuring the tissue parameters of interest, and further comprising an evaluation unit.

DESCRIPTION OF THE PRIOR ART

The paper "A microdialysis method allowing characterization of intercellular water space in humans", by P. Lönnroth, P.-A. Jansson, U. Smith, in "Dialysis of Human Tissue In Vivo", American Physiological Society, 1987, pp 228–231, discusses the use of thin, flexible tubes which Call be implanted in the tissue, for instance, for analyzing the glucose content of the cell fluid. The wail of this kind of microdialysis tube is permeable to the substance to be analyzed, permitting it to diffuse into the interior of the tube. Due to the separating wall of the tube the risk of infection is kept comparatively small. For analysis of the interesting substance a sensor may be introduced into the microdialysis tube from outside, or the tube is flushed with the fluid which is then analyzed outside. A disadvantage of this measuring technique, by means of which comparatively large tissue areas may be examined, is that it will only yield mean values of concentration over the entire surface of the tube subject to the sample medium, so that local variations cannot be detected.

In surgical applications it is often necessary not only to check on arterial blood gases but to monitor the blood and oxygen supply of an internal organ during and after surgery, for example. In this context it has proved possible to determine the state of oxygen supply by measuring local oxygen pressure in the tissue. A suitable method would be polarographic measurement of a $pO_2$ histogram by means of a thin needle electrode covered by a membrane, for instance. The $pO_2$ histogram includes a large number of individual readings taken at various places in the tissue. Since this method is not suitable for continuous monitoring, however, continuously measuring polarographic $pO_2$ catheter electrodes are inserted into the tissue, whose exterior diameter is only about 0.55 mm, for example. The disadvantage of these electrodes is that they measure $pO_2$ only in one particular place in the tissue, which need not necessarily be the best for reflecting the overall situation.

Another disadvantage of such polarographic electrodes is that they only permit measurement of relative $pO_2$ values. The calibration curve obtained in gas or salt solutions cannot be applied to measurements in human or animal tissue, as the parameters determining the slope of the calibration curve will vary widely in the tissue and cannot be predicted with certainty for this reason.

In AT-B 392 539 optical sensors are described comprising a light guide and an indicator substance immobilized thereon, which are not suitable, however, for measuring concentration profiles in tissues. The description discloses a sensor for optical determination of the catalytic enzyme activity of a sample, in which an enzyme substrate is applied on the exterior surface of the cylindrical core of a light guide. During the measuring process the tip of the sensor is immersed in the sample solution.

SUMMARY OF THE INVENTION

It is an object of the invention to propose a sensing device which permits continuous determination of the local concentration of a certain species or the concentrations of different analytes, i.e., simultaneously in several places of the tissue, in order to reflect the heterogeneity of the tissue.

In the invention this object is achieved by providing that the tube have several areas along its length which contain either identical or different optically excitable and readable, preferably luminescence-optical, indicating substances for measuring the local distribution of one parameter, such as $O_2$ concentration or $O_2$ partial pressure, or for simultaneous measurement of at least two different parameters, belonging to the $pO_2$, $pCO_2$, pH group, for example. The term tube may also refer to a tube system composed of flexible and rigid parts, each part offering the necessary strength, permeability and transparency for a particular application. The indicators may be applied on the circumference of the tube in ring-type fashion, or only in individual sites on the surface of the tube, or they may be integrated into the tube. Optical readings of indicators placed on the outside of the tube will necessitate an optically transparent tube material. The wall of the tube may be impermeable to the analyte(s) while admitting other substances. If the indicator is provided inside the tube or integrated into the tube, the wall of the tube must be permeable to the analyte(s) as well. With the use of this kind of sensing device a number of measuring sites in the tissue may be covered by means of a single measuring tube, thus minimizing tissue trauma. Suitable indicating substances include absorption indicators, luminescence indicators, and chemiluminescence indicators.

For simultaneous determination of the absolute values of an analyte concentration in several places or depths of the tissue, the use of different indicators for measuring one and the same species may be proposed for the sensing device of the invention. By isolating the signals the concentration profile or the local distribution of an analyte may be obtained. In this way the heterogeneity of the tissue may be continuously taken into account. Indicator systems may consist of identical or different indicator substances or of enzyme-indicator combinations.

The individual areas may also be provided with different indicator substances for simultaneous measurement of at least two concentration values taken from the $pO_2$, $pCO_2$, pH group, for example. Furthermore, a combination of indicator substances may be placed inside or on the biocompatible tube. A combination of $pO_2$ and pH indicators may be of advantage, as a reduced oxygen supply is accompanied by a drop in pt, for instance. With the use of suitable indicator systems other interesting substances in the tissue may be measured, such as potassium, calcium, glucose, hormones and anesthetic gases. The signals emitted by the individual indicators as a function of analyte concentration may be isolated by optical means, for example, suitable filters, and processed separately.

The device could also be combined with other sensors. By measuring the temperature inside the tissue, for instance, or pressure, electric activity, radioactivity, or hydrogen clearance, important additional information may be obtained.

In those variants of the device in which the excitation light is guided in the light guide by total reflection, provisions will have to be made so that the excitation light can leave the light guide in the area of the indicating substances, unless excitation is induced by the evanescent component of the excitation light, as is described in U.S. Pat. No. 3,604,927, for example.

Passage of the excitation radiation from the optical waveguide into the indicator layer may also be effected by suitable selection of the refractive index of the indicator layer (cf. DE-C2 35 32 563).

In an advantageous variant it is proposed that the wall of the tube be configured as a light guide. This will provide a simple method of simultaneously performing local optical measurements in the wall of the tube and mean value measurements of the analytes diffusing into the interior of the tube. Such simultaneous local and global measurement will also be possible if the refractive index of the tube wall is lower than that of a liquid, gel-like or solid filling of the tube, so that the light is guided in the substance filling the tube. The analytes diffusing into the liquid filling can be drained off and analyzed in a conventional way.

If the necessary rigidity for puncturing the tissue is not ensured, the invention provides that tile tube be surrounded by a hollow needle, which can be removed after the tube is inserted in the tissue.

Another advantageous variant of the invention proposes that the end of the tube located in the tissue be mirror-faced and the other end be used for feeding in the excitation radiation and picking tip the measurement radiation in a known manner.

In further development of the invention the proposal is put forward that the tribe be threaded through the tissue so that both ends project from the surface of the tissue, one end being available for feeding in the excitation radiation, and the other one for picking up the measurement radiation. It would also be possible, however, to rise one and the same end of the tube for entering the excitation radiation and picking up the measurement radiation, while the other end is used for other medical purposes, such as feeding in substances to provoke a test reaction.

For the purpose of measuring the surface concentration of a given species it is proposed that at least one of the free ends of the tube be provided with an optode foil in contact with the surface of the tissue.

In another advantageous version of the invention the light guide is configured as a probe with one or more mirror faces inclined towards the longitudinal axis by about 45°, i.e., preferably dichroitic mirrors, which probe is inserted into the tube in axial direction. With the use of the probe indicator readings will be taken automatically, the probe being put into position by means of a pulling device or spindle.

For measurement in bone tissues or joints a steel tube or a cannula with perforations in its wall could be used. The sensors or indicators located in the perforations may be read by a probe to be introduced into the cannula.

In a preferred variant of the invention the tube is transparent in at least one area. In this way tissue observations may be performed and indicators located outside of the tube may be optically detected. Such indicators present in the tissue include haemoglobin, myoglobin, or the fluorescent NADH enzyme of the respiratory chain.

The optical waveguide introduced into the tissue need not be in direct contact with an optical excitation and evaluation unit, but the invention may provide that a known device be used for contact-free feeding of excitation radiation and pick-up of measurement radiation, which includes the evaluation unit.

Contact-free measurement of optical signals on moving surfaces is described in "Oxygen Transport To Tissue VIII", N. Opitz and D. W. Lübbers, Adv. Exp. Med. Biol. 200, 367–371, Plenum Press, 1986.

As human and animal tissues, in particular the skin, are characterized by good transparency to optical radiation in the red and infrared ranges, the invention permits the use of an indicator substance whose excitation/emission radiation has a wavelength of 600 to 1,200 nm, approximately. In this instance the sensor is excited and read from outside the tissue, for example by sensors or sensing layers on the surface of the skin.

To improve tissue analysis it is of advantage if the tube, at least in parts, is made of material accumulating the sample substance. Silicone materials, for instance, are known to accumulate various substances, such as $CO_2$ or anesthesia gases, so that even small concentrations of these substances can be measured precisely,

DESCRIPTION OF THE DRAWINGS

Following is a more detailed description of the invention, with reference to the accompanying drawings, in which FIG. 1 shows a sensing device as described by the invention, FIGS. 2 and 3 show variants of this device, FIGS. 4 to 9 give detailed views of microdialysis tubes using different signal transmission methods, all in accordance with the invention.

DESCRIPTION OF THE PREFERRED EMBODIMENTS

Figure 4:
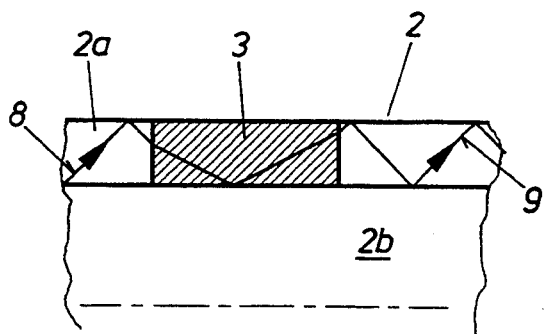

FIG. 1 presents a sensing device for measuring local concentrations of a species in human or animal tissue, with a thin, biocompatible tube (or cannula) 2 for insertion into the tissue 1, along whose longitudinal axis 22 several areas 3 to 5 are provided within which indicators having different optical properties are immobilized. If the tube itself, for example, a microdialysis tube, does not have the necessary rigidity, a hollow needle 6 may be provided for inserting the tube 2 into the tissue, which needle 6 can be removed after pucturing. The tube 2 of the sensor may be directly connected with a light source and a detector, or—as shown in FIG. 1—it may be provided with a unit 7 for contact-free feeding of the excitation radiation 8 and pick-up of the measurement radiation 9. In addition to a radiation source 10 and a detector 11, the unit 7 contains a beam splitter 12 for separating the measurement radiation from the excitation radiation and an evaluation device 13 connected to the detector 11. In this variant the end 14 of the tube 2 remaining in the tissue 1 carries a mirror-coated cap 15, while the free end 16 is next to the feed unit 7.

FIG. 2 shows a variant of the sensor in FIG. 1, the free end 16 of the tube 2 being surrounded by an optode foil 17, which is in contact with the tissue surface 18 and measures the surface concentration of a species (for example, $pO_2$ distribution).

FIG. 3 shows a variant in which the tube 2 is threaded through the tissue 1, one end 14 being available for introducing the excitation radiation 8 and the other end 16 for picking up the measurement radiation 9.

Figure 5:
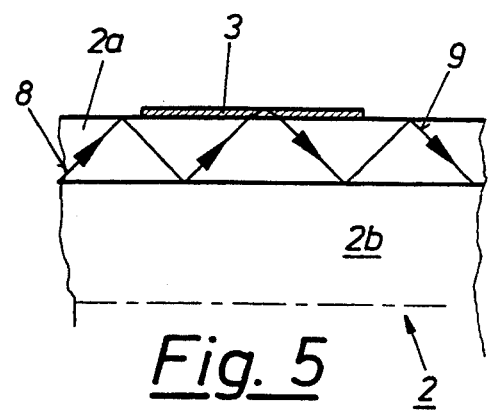

In FIGS. 4 and 5 light is guided only in the tube wall 2a. The indicators either are integrated in the tube wall 2a, where they are passed through by the excitation radiation 8 or the measurement radiation 9 (FIG. 4), or they are applied on the tube wall 2a, reflecting the excitation radiation 8 or the measurement radiation 9 (FIG. 5).

Figure 6:
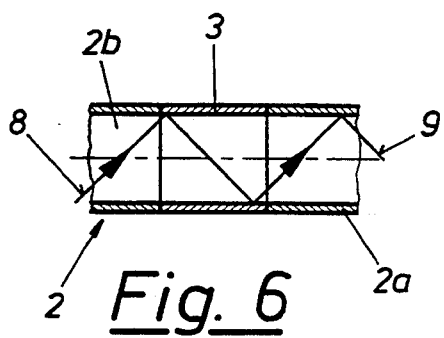
Figure 7:
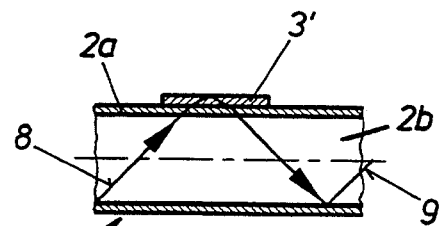

By suitably matching the refractive indices of tube wall 2a and tube filling 2b most of the light can be guided in the tube filling 2b, as is shown in FIGS. 6 and 7. Again, the indicator substance of an area 3 either is integrated in the tube wall 2a (FIG. 6) or it is applied on the surface of the tube wall (FIG. 7).

Figure 8:
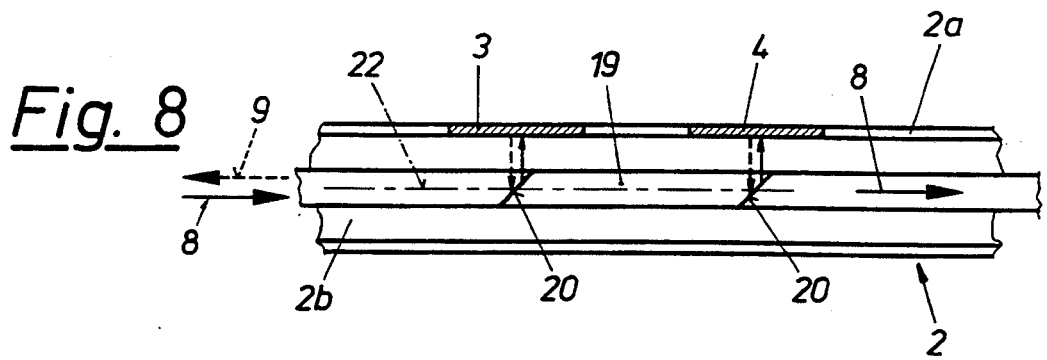

Transmission of the light signals could also be implemented by a probe 19 which is inserted into the tube 2 (cf FIG. 8). For taking indicator readings several dichroitic mirrors 20 are provided which are mounted on the probe 19 one behind the other. In this way several indicators may be monitored simultaneously in one and the same position of the probe 19.

For applications in bone tissues or joints a cannula 20 with perforations in areas 3 to 5 could be used, the indicator substances being provided in these perforations.

Figure 9:
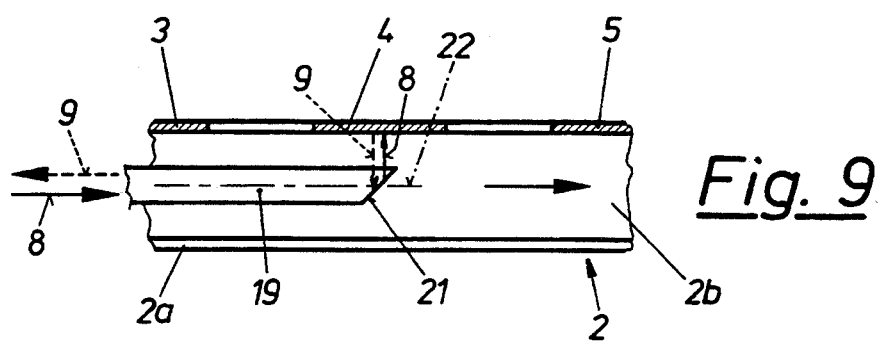

As is shown in FIG. 9, indicator readings also may be taken serially, in which case the probe 19 is only provided with a single mirror face 21. The mirror 21 must be positioned in the vicinity of the particular indicator substance to be read. After transmission of the data, the probe is axially moved towards the next area 3,4,5 containing another indicator.

Apart from tissue analysis the sensing device presented in this paper may be used to advantage in other technological or scientific applications, for example, for monitoring a bioreactor or determining the water quality of a lake or river.

We claim:

1. An optical sensing device comprising a thin biocompatible tube having a tube wall and a longitudinal axis, said tube being insertable into human or animal tissue, wherein said biocompatible tube operates as a single light guide and has several areas axially displaced which contain different optically excitable and readable indicating substances, and further comprising means for exciting and reading said indicating substances.

2. An optical sensing device comprising a thin biocompatible tube having a tube wall and a longitudinal axis, said tube being insertable into human or animal tissue, wherein said tube is provided with a liquid, gel-like or solid tube filling, wherein the refractive index of said tube wall is lower than the refractive index of said tube filling, so that said tube filling operates as a single light guide and wherein said tube has several areas axially displaced which contain different, optically excitable and readable indicating substances, and further comprising means for exciting and reading said indicating substances.

3. A sensing device according to claims 1 or 2, wherein said tissue parameter is the $O_2$ concentration or the $O_2$ partial pressure.

4. A sensing device according to claims 1 or 2, wherein said at least two tissue parameters belong to the $pO_2$, $PCO_2$, pH group.

5. A sensing device according to claims 1 or 2, wherein said biocompatible tube is a microdialysis tube.

6. A sensing device according to claims 1 or 2, wherein said indicating substances are luminescence-optical substances.

7. A sensing device according to claims 1 or 2, wherein said tube is surrounded by a hollow needle, which is removable after said tube is inserted into human or animal tissue.

8. A sensing device according to claims 1 or 2, wherein one end of said biocompatible tube located in said tissue is mirror-faced and the other end is used for feeding in excitation radiation and picking up measurement radiation.

9. A sensing device according to claims 1 or 2, wherein said biocompatible tube is threadable through said tissue having both ends of said tube projecting from a tissue surface, one end of said tube being available for feeding in excitation radiation and the other end for picking up measurement radiation.

10. A sensing device according to claims 1 or 2, wherein at least one free end of said tube is provided with an optode foil in contact with said tissue surface for measuring the surface concentration of a given species.

11. A sensing device according to claims 1 or 2 comprising a probe with at least one mirror face inclined towards said longitudinal axis of said tube by about 45°, wherein said probe is insertable into said tube in axial direction.

12. A sensing device according to claim 11, wherein each said mirror face is a dichroitic mirror.

13. A sensing device according to claims 1 or 2, wherein said biocompatible tube is transparent in at least one area.

14. A sensing device according to claims 1 or 2, comprising means for contact-free feeding in excitation radiation and pick-up measurement radiation to said biocompatible tube, wherein said means includes an evaluation unit.

15. A sensing device according to claims 1 or 2, comprising indicating substances with an excitation and emission wavelength of about 600 to 1200 nm.

16. A sensing device according to claims 1 or 2, wherein at least parts of said biocompatible tube are made of material accumulating a sample substance to be measured.

* * * * *